United States Patent [19]

Wade

[11] Patent Number: 4,473,570

[45] Date of Patent: Sep. 25, 1984

[54] IMIDAZO[1,5-C]PYRIMIDIN-5-ONES

[75] Inventor: James J. Wade, Oakdale, Minn.

[73] Assignee: Riker Laboratories, Inc., St. Paul, Minn.

[21] Appl. No.: 519,672

[22] Filed: Aug. 2, 1983

[51] Int. Cl.$^3$ .................. C07D 487/14; A61K 31/505
[52] U.S. Cl. .................................... 424/251; 544/281; 544/310; 544/312; 544/313
[58] Field of Search ......................... 544/281; 424/251

[56] References Cited

U.S. PATENT DOCUMENTS 4,152,427 5/1979 Maurer et al. ...................... 544/281
4,153,695 5/1979 Turner .................................. 544/281

Primary Examiner—Donald G. Daus
Assistant Examiner—S. A. Gibson
Attorney, Agent, or Firm—Donald M. Sell; James A. Smith; Robert W. Sprague

[57] ABSTRACT

Imidazo[1,5-c]pyrimidin-5-ones have been found to have potent bronchodilator activity. Pharmacological methods of using these compounds and pharmaceutical compositions containing these compounds are also disclosed.

13 Claims, No Drawings

IMIDAZO[1,5-C]PYRIMIDIN-5-ONES

TECHNICAL FIELD

The present invention relates to compounds which are named imidazo[1,5-c]pyrimidin-5-ones. This invention also relates to the pharmacological use of these compounds as bronchodilators and to pharmaceutical compositions containing these compounds.

BACKGROUND OF THE INVENTION

Applicant is unaware of any imidazo[1,5-c]pyrimidin-5-ones which have been reported in the literature.

DETAILED DESCRIPTION OF THE INVENTION

The present invention relates to novel imidazo[1,5-c]pyrimidin-5-ones which are useful bronchodilators. The present invention also relates to pharmacological methods of using these compounds as bronchodilators, and to pharmaceutical compositions containing these compounds.

More specifically, the present invention relates to compounds of Formula I

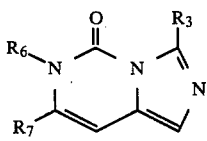

wherein $R_3$ is hydrogen, lower alkyl or phenyl; $R_6$ is hydrogen, lower alkyl or benzyl; and $R_7$ is chloro, lower alkoxy, lower alkylthio or methyl; and pharmaceutically acceptable acid-addition salts thereof.

The phrase "lower alkyl" is defined for purposes of the instant specification and claims as designating straight and branched chain alkyl groups containing one to four carbon atoms. Preferred lower alkyl substituents are methyl, ethyl and propyl.

One presently preferred sub-class of compounds of the invention is that wherein $R_7$ is lower alkoxy or lower alkylthio. Another preferred subclass is that wherein $R_6$ is lower alkyl or benzyl. These compounds are preferred because of generally higher potency in protection against histamine-induced contraction of isolated guinea pig tracheal tissue. This assay is discussed in greater detail below.

Specific preferred compounds which are active at a concentration of 10 ug per ml or lower in the above assay are:
3-methyl-7-methylthio-6-(n-propyl)imidazo[1,5-c]pyrimidin-5-one
3-methyl-7-methylthioimidazo[1,5-c]pyrimidin-5-one
7-chloro-3-(n-propyl)imidazo[1,5-c]pyrimidin-5-one
7-chloro-3-methyl-6-(n-propyl)imidazo[1,5-c]pyrimidin-5-one
3,7-dimethyl-6-(n-propyl)imidazo[1,5-c]pyrimidin-5-one
6-benzyl-3,7-dimethylimidazo[1,5-c]pyrimidin-5-one
6-benzyl-3-methyl-7-methylthioimidazo[1,5-c]pyrimidin-5-one
3,6-dimethyl-7-methylthioimidazo[1,5-c]pyrimidin-5-one The bronchodilator activity of the compounds of the invention was assessed by the measurement of effects on isolated tracheal spirals. This is a well-known in vitro test for determining bronchodilator activity. The test was conducted as follows: Female guinea pigs were sacrificed, and each trachea was removed and cut into a spiral strip. Each strip was mounted in a constant temperature (37° C.) muscle bath of approximately 15 ml volume. The bathing medium was Krebs-Henseleit solution. Movement of the tracheal strip was measured by a means of an isometric transducer connected to an electric recorder. The bath was aerated with a mixture of 95% carbon dioxide and 5% oxygen. Contractions were induced in the strips by the addition of a suitable amount of histamine, acetylcholine or barium chloride. The amount of a given compound of the invention (measured in ug/ml) required to provide greater than 75% relaxation of the drug-induced contraction is considered an effective concentration. For comparison, a well known standard bronchodilator, aminophylline, requires concentrations of 50 ug/ml versus histamine, 100 ug/ml versus acetylcholine and 10 ug/ml versus barium chloride induced contraction.

The compounds of the invention which were found to be most active in the in vitro test, including some of those listed as preferred compounds, were tested in vivo in the guinea pig for oral activity using the so-called histamine aerosol method as described in U.S. Pat. No. 3,248,292. This test was modified slightly in that a 0.1% aqueous solution of histamine was used as the agent for inducing bronchial constriction. Oral doses were measured in mg/kg of body weight of the guinea pig.

The compounds of the invention may be administered to mammals in order to obtain bronchodilation. The compounds may be administered orally, parenterally or by inhalation. The usual effective human dose will be 0.1 to 50 mg/kg of body weight.

Pharmaceutically acceptable acid-addition salts of compounds of Formula I are generally prepared by reaction of the respective compound with an equimolar amount of a relatively strong acid, preferably an inorganic acid such as hydrochloric, sulfuric or phosphoric acid in a polar solvent. Isolation of the salt is facilitated by the addition of a solvent in which the salt is insoluble, an example of such a salt being diethyl ether.

The compounds of this invention, either as free bases or in the form of a pharmaceutically acceptable acid-addition salt, can be combined with conventional pharmaceutical diluents and carriers to form such dosage forms as tablets, capsules, suspensions, solutions, suppositories and the like. The pharmaceutical carrier employed may be, for example, either a solid or liquid. Examples of suitable solid carriers are lactose, terra alba, sucrose, talc, gelatin, agar, pectin, acacia, magnesium stearate, stearic acid, and the like. Examples of suitable liquid carriers are syrup, peanut oil, olive oil, water and the like. Similarly, the carrier or diluent can include any time delay material well known to the art, such as glyceryl monostearate or glyceryl distearate, these being useful alone or, for example, in combination with a wax.

Compounds of Formula I wherein $R_3$ and $R_6$ are as defined above; and $R_7$ is lower alkoxy or lower alkylthio may be prepared as follows in Reaction Scheme I.

Reaction Scheme I

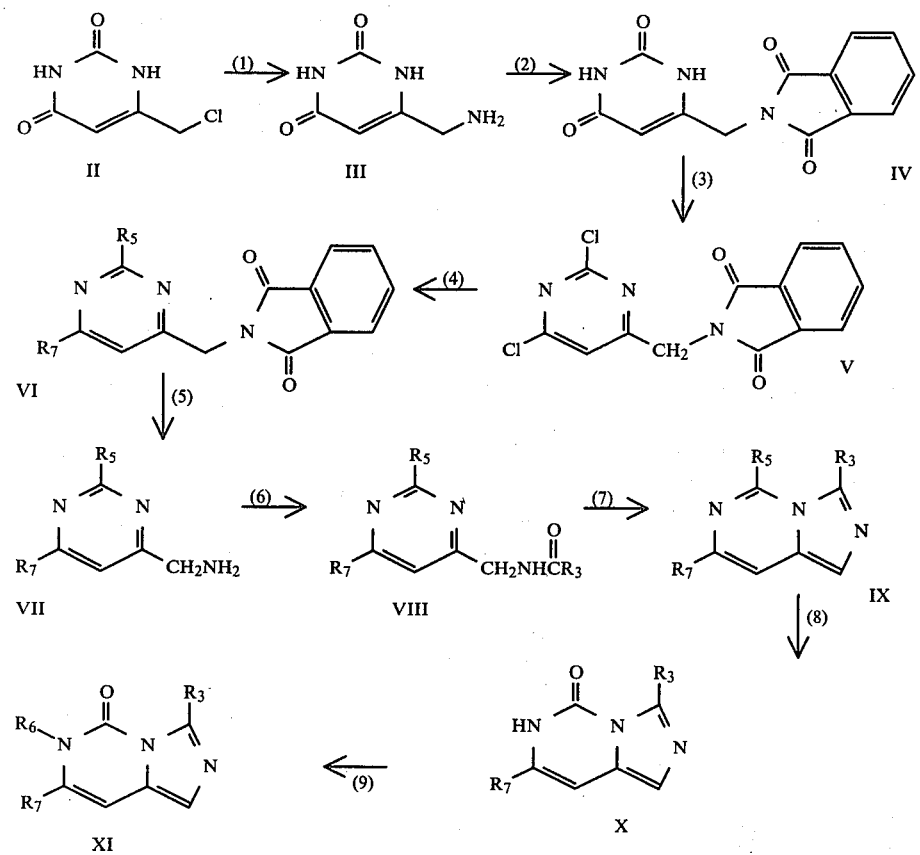

In step (1) of Reaction Scheme I, the known compound of Formula II is reacted with anhydrous ammonia to provide the compound of Formula III.

In step (2), the compound of Formula III is reacted with phthalic anhydride to provide an intermediate of Formula IV. This reaction is carried out in a solvent such as N,N-dimethylformamide and preferably also in the presence of a basic catalyst such as triethylamine.

In step (3), the intermediate of Formula IV is reacted with excess phosphorous oxychloride to provide an intermediate of Formula V.

The intermediate of Formula V is reacted in step (4) with an alkali metal alkoxide or an alkali metal alkylthiolate to provide a pyrimidine of Formula VI wherein $R_5$ and $R_7$ are lower alkoxy or lower alkylthio.

In step (5), the compound of Formula VI is reacted with hydrazine in the presence of an inert solvent such as a lower alkanol or dioxane to provide the compound of Formula VII. The reaction is carried out by refluxing the reaction mixture.

The compound of Formula VII is acylated in step (6) using conventional methods such as reaction of the compound with an organic acid, an organic acyl halide or an organic acyl anhydride which will introduce the desired $R_3$ moiety into the molecule. The product of step (6) is an intermediate of Formula VIII.

In step (7), the intermediate of Formula VIII is cyclized to provide a compound of Formula IX. The cyclization reaction is preferably carried out by heating the intermediate in the presence of one equivalent of phosphorous oxychloride and solvent. Examples of suitable solvents which may be used are dioxane, 1,2-dimethoxyethane, tetrahydrofuran, benzene and the like. The reaction of step (7) may also be carried out in the presence of excess phosphorous oxychloride. In that case, use of a solvent is optional although generally preferred.

In step (8), the intermediate of Formula IX is reacted with one equivalent of an alkali metal alkoxide such as sodium methoxide to provide a compound of the invention of Formula X (wherein $R_6$ of Formula I is hydrogen). This reaction is carried out by heating the reactants in the presence of the alcohol from which the alkali metal alkoxide is derived (e.g., methanol where sodium methoxide is employed).

When $R_5$ and $R_7$ are alkoxy and when excess phosphorous oxychloride is used and vigorous reaction conditions such as extended reaction times are employed, the reaction of step (7) is generally followed by the reaction of step (8) without isolation of the compound of Formula IX and without the addition of alkoxide. The extent of reaction and the relative amounts of compounds of Formula IX and X is conveniently monitored by thin layer chromatographic analysis.

In step (9), the compound of Formula X is reacted, in the presence of a strong base such as sodium hydride, with a lower alkyl halide or benzyl halide to provide a compound of the invention of Formula XI wherein $R_6$ is lower alkyl or benzyl, respectively.

Compounds of Formula I wherein $R_3$ and $R_6$ are as defined above; and $R_7$ is chloro, may be prepared as follows in Reaction Scheme II:

Reaction Scheme II

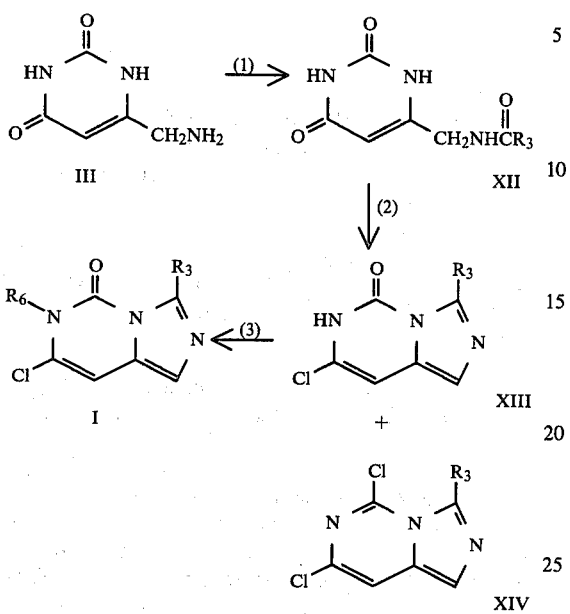

In step (1) of Reaction Scheme II, the compound of Formula III is acylated in accordance with step (5) of Reaction Scheme I to provide an intermediate of Formula XII.

In step (2), the intermediate of Formula XII is cyclized by refluxing in the presence of an excess of phosphorous oxychloride. The mixture of compounds of Formula XIII and XIV thereby obtained may then be separated by conventional methods such as extraction, recrystallization and chromatography to provide pure compound of Formula XIII of the invention.

The compound of Formula XIII may be further reacted in step (3) using the method of step (9) of Reaction Scheme I to provide other compounds of Formula I wherein $R_6$ is lower alkyl or benzyl.

Compounds of Formula I wherein $R_3$ and $R_6$ are as defined above; and $R_7$ is methyl may be prepared as follows in Reaction Scheme III:

Reaction Scheme III

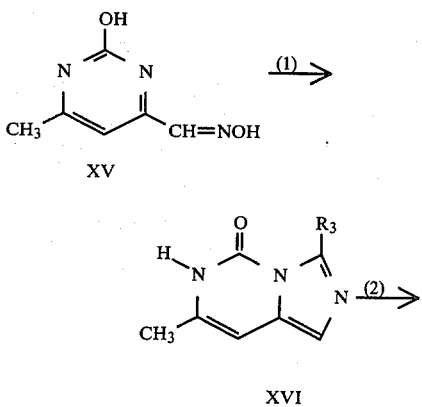

-continued
Reaction Scheme III

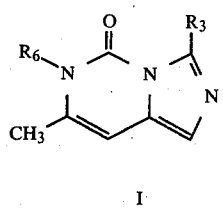

In Reaction Scheme III, the known compound of Formula XV is reduced with stannous chloride in concentrated hydrochloric acid. Then, without isolation, the tin salt intermediate is treated with an excess of a carboxylic acid anhydride such as acetic anhydride in the presence of a corresponding alkali metal carboxylic acid salt (e.g., sodium acetate where the anhydride employed is acetic anhydride). The product of step (1) is a compound of Formula XVI.

The compound of Formula XVI may be further reacted in step (2) using the method of step (9) of Reaction Scheme I to provide other compounds of Formula I wherein $R_6$ is lower alkyl or benzyl.

The following examples are provided to illustrate the synthetic methods used in the invention. They are not intended to limit the scope of the invention.

EXAMPLE 1

Synthesis of 3-Methyl-7-methylthioimidazo[1,5-c]pyrimidin-5-one

Part A

A mixture of 100 g (0.623 mole) of 6-chloromethylpyrimidine-2,4-dione and 200 ml of anhydrous ammonia was allowed to react overnight in a sealed bomb at about 20° C. The solid residue was slurried in ethyl acetate, separated by filtration, and washed sequentially with water and methanol to provide 6-aminomethylpyrimidine-2,4-dione, m.p. 295°–297° C.

Part B

To a mixture of 10.0 g (70.9 mmole) of 6-aminomethylpyrimidine-2,4-dione and 11.0 g (74.3 mmole) of phthalic anhydride in 80 ml of N,N-dimethylformamide was added 0.2 ml of triethylamine while heating at 120° C. After 2.5 hours the mixture was poured into 400 ml of an ice-water mixture. The solid was separated by filtration, washed with water and ethanol, and dried. The white solid was 6-phthalimidomethylpyrimidine-2,4-dione.

Part C

A mixture of 2.3 g (8.3 mmole) of 6-phthalimidomethylpyrimidin-2,4-dione and 50 ml of phosphorous oxychloride was heated to reflux for 4.5 hours and then cooled. The mixture was partially evaporated, poured into 300 ml of ice-water, and neutralized with solid sodium bicarbonate. The yellow solid was 2,4-dichloro-6-phthalimidomethylpyrimidine. Analysis: Calculated for $C_{13}H_7Cl_2N_3O_2$: %C, 50.67; %H, 2.29; %N, 13.64; Found: %C, 50.1; %H, 2.0; %N, 13.4. The structural assignment was confirmed by infrared and nuclear magnetic resonance spectral analyses.

Part D

To a stirred solution of sodium methoxide (prepared in 600 ml of methanol from 10.0 g (0.43 mole) of sodium metal) was added 32 ml (0.58 mole) of methanethiol and 50 g (0.162 mole) of 2,4-dichloro-6-phthalimidomethylpyrimidine. The mixture was heated at reflux for about 20 hours, then cooled. The solid was separated by filtration, and washed with water and a small amount of methanol to provide a tan solid. This product was 2,4-bis(methylthio)-6-phthalimidomethylpyrimidine. The structural assignment was confirmed by infrared and nuclear magnetic resonance spectral analyses.

Part E

To a mixture of 20 g (60.4 mmole) of 2,4-bis(methylthio)-6-phthalimidomethylpyrimidine in 125 ml of ethanol and 125 ml of dioxane was added 3.5 g (70 mmole) of hydrazine hydrate, and the mixture was heated at reflux for 20 hours. The mixture was evaporated and the residue was added to 350 ml of water. To this mixture was added 10 ml of concentrated hydrochloric acid and the mixture was stirred and heated at reflux for 30 minutes. The mixture was cooled and the solid phthalhydrazide was removed by filtration. The filtrate was neutralized with ten percent aqueous sodium hydroxide solution and extracted with four 200 ml portions of chloroform. The chloroform extracts were washed with three 100 ml portions of water and 100 ml of saturated aqueous sodium chloride solution, and were dried over magnesium sulfate. Evaporation provided a residue which solidified to light yellow solid 6-aminomethyl-2,4-bis(methylthio)pyrimidine.

Part F

A mixture of 11 g (16.5 mmole) of 6-aminomethyl-2,4-bis(methylthio)pyrimidine and 75 ml of acetic anhydride was stirred at room temperature for 16 hours, then evaporated. The residue was isolated by filtration and washed with a small amount of methanol to provide white solid 6-acetylaminomethyl-2,4-bis(methylthio)-pyrimidine. The structural assignment was supported by infrared spectral analysis.

Part G

To a stirred suspension of 9.00 g (37.0 mmole) of 6-acetylaminomethyl-2,4-bis(methylthio)pyrimidine in 100 ml of dioxane under nitrogen was added 7.00 g (45.7 mmole) of phosphorous oxychloride. The mixture was heated at reflux for one hour, then cooled. The solid product, 5,7-bis-(methylthio)-3-methylimidazo[1,5-c]pyrimidine hydrochloride, was separated by filtration and washed with diethyl ether. This salt was mixed with 200 ml of water, and the mixture was then basified with solid sodium bicarbonate and extracted with five 50 ml portions of chloroform. The combined extracts were washed sequentially with 50 ml of water and two 50 ml portions of saturated aqueous sodium chloride solution, and were then dried over magnesium sulfate. Evaporation provided a residue which was recrystallized with treatment with decolorizing charcoal from 1:1 benzene/hexanes. The product was bright yellow solid 5,7-bis(methylthio)-3-methylimidazo[1,5-c]-pyrimidine, m.p. 124°–126° C. Analysis: Calculated for $C_9H_{11}N_3S_2$: %C, 48.0; %H, 4.9; %N, 18.7; Found: %C, 48.4; %H, 4.7; %N, 19.1.

Part H

To a solution of 4.8 g (21.3 mmole) of 5,7-bis(methylthio)-3-methylimidazo[1,5-c]pyrimidine in 10 ml of water and 90 ml of methanol was added 5.0 g (23.1 mmole) of 25% sodium methoxide in methanol. The mixture was heated at reflux for 16 hours, poured into 400 ml of an ice-water mixture, and acidified with 3 ml of concentrated hydrochloric acid. The mixture was basified with solid sodium bicarbonate, and the precipitate was separated by filtration. The solid was washed with water and dried to provide 3-methyl-7-methylthioimidazo[1,5-c]pyrimidin-5-one, m.p. 221°–222° C.

Analysis: Calculated for $C_8H_9N_3OS$; %C, 49.2; %H, 4.7; %N, 21.5; Found; %C, 48.9; %H, 4.6; %N, 21.6.

EXAMPLE 2

Synthesis of 7-Methoxy-3-methylimidazo[1,5-c]pyrimidin-5-one

Part A 2,4-Dichloro-6-phthalimidomethylpyrimidine was converted to 2,4-dimethoxy-6-phthalimidomethylpyrimidine by refluxing with sodium methoxide in methanol.

Part B

Using the method of Part E, Example 1, 2,4-dimethoxy-6-phthalmidomethylpyrimidine was converted to 6-aminomethyl-2,4-dimethoxypyrimidine.

Part C

Using the method of Part F, Example 1, 6-aminomethyl-2,4-dimethoxypyrimidine was converted to 6-acetylaminomethyl-2,4-dimethoxypyrimidine.

Part D

To a suspension of 3.2 g (15.2 mmole) of 6-acetylaminomethyl-2,4-dimethoxypyrimidine in 50 ml of dioxane was added 2.90 g (18.9 mmole) of phosphorous oxychloride. The mixture was stirred at 20° C. for four days, then heated at its reflux temperature for two hours. The mixture was poured into 100 ml of water, the solution was neutralized with solid sodium bicarbonate and 100 ml of chloroform was added. The aqueous phase was separated from the organic phase and solid residue and extracted thrice with 100 ml portions of chloroform. The extracts were combined with the organic phase and solid residue and washed with saturated aqueous sodium chloride solution and dried over magnesium sulfate. Evaporation provided a residue which was extracted with 300 ml of boiling isopropanol. The solution was treated with decolorizing charcoal, then partially evaporated to about 100 ml and cooled. The solid separated by filtration was 7-methoxy-3-methylimidazol[1,5-c]pyrimidin-5-one, m.p. 228° C. (dec.). Analysis: Calculated for $C_8H_9N_3O_2$: %C, 53.6; %H, 5.1; %N, 23.5; Found: %C, 53.2; %H, 5.0; %N, 23.7.

EXAMPLE 3

Synthesis of 7-Methylthio-3-phenylimidazo[1,5-c]pyrimidin-5-one

Part A

A mixture of benzoyl chloride and 6-aminomethyl-2,4-bis(methylthio)pyrimidine (from Part E, Example 1) was converted to 6-benzoylaminomethyl-2,4-bis(methylthio)pyrimidine by heating in chloroform in the presence of triethylamine as an acid acceptor.

Part B

Using the method of Part G, Example 1, 6-benzoylaminomethyl-2,4-bis(methylthio)pyrimidine was cyclized to provide yellow solid 5,7-bis(methylthio)-3-phenylimidazo[1,5-c]pyrimidine, m.p. 117°–118° C. after recrystallization from cyclohexane. Analysis: Calculated for $C_{14}H_{13}N_3S_2$: %C, 58.5; %H, 4.6; %N, 14.6; Found: %C, 58.9; %H, 4.4; %N, 14.7.

Part C

Using the method of Part H, Example 1, 5,7-bis(methylthio)-3-phenylimidazo[1,5-c]pyrimidine was reacted with aqueous sodium methoxide to provide 7-methylthio-3-phenylimidazo[1,5-c]pyrimidin-5-one, m.p. 198°–199° C. Analysis: Calculated for $C_{13}H_{11}N_3OS$: %C, 60.7; %H, 4.3; %N, 16.3; Found: %C, 60.7; %H, 4.1; %N, 16.7.

EXAMPLE 4

Synthesis of 7-Chloro-3-methylimidazo[1,5-c]pyrimidin-5-one

Part A

To a mixture of 4-aminomethylpyrimidine-2,6-dione in 50 ml of acetic anhydride was added two drops of concentrated sulfuric acid. The mixture was heated on a steam bath for one hour, and was then stirred overnight at about 20° C. The precipitate was separated by filtration, washed sequentially and thoroughly with water and methanol, and dried. The product was white solid 4-acetylaminomethylpyrimidine-2,6-dione. The structural assignment was confirmed by infrared and nuclear magnetic resonance analyses.

Part B

A suspension of 6.63 g (36.2 mmole) of 4-acetylaminomethylpyrimidine-2,6-dione in 250 ml of phosphorous oxychloride was heated at reflux for 20 hours, and was cooled and evaporated. The residue was added to about 700 ml of cold saturated sodium bicarbonate solution. To the resulting mixture was added 200 ml of chloroform and enough solid sodium bicarbonate to neutralize the mixture. The solid was separated by filtration, washed with water and ethanol, and recrystallized from ethanol to provide yellow solid 7-chloro-3-methylimidazo[1,5-c]pyrimidin-5-one, m.p. 239° C. (dec.). Analysis: Calculated for $C_7H_6ClN_3O$; %C, 45.8; %H, 3.3; %N, 22.9; Found; %C, 45.8; %H, 3.1; %N, 22.8.

EXAMPLE 5

Synthesis of 7-Chloro-3-(n-propyl)imidazo[1,5-c]pyrimidin-5-one

Part A

Using the method of Part A, Example 4, 4-aminomethylpyrimidine-2,6-dione was converted to 4-(n-butyryl)aminomethylpyrimidine-2,6-dione.

Part B

A suspension of 7.15 g (33.9 mmole) of 4-(n-butyryl)aminomethylpyrimidine-2,6-dione in 50 ml of phosphorous oxychloride was heated first at 75° C. for six hours and then at reflux for 16 hours. The solution was evaporated and the residue was mixed with 200 ml of an ice-water mixture. The mixture was partly neutralized with concentrated ammonium hydroxide and was then completely neutralized with solid sodium bicarbonate. The mixture was extracted with six 100 ml portions of chloroform. The combined extracts were washed twice with 200 ml of distilled water, once with 200 ml of saturated aqueous sodium chloride solution, dried over magnesium sulfate, and treated with decolorizing charcoal. Evaporation provided a solid residue. The residue was extracted twice with boiling cyclohexane to remove 5,7-dichloro-3(n-propyl)imidazo[1,5-c]pyrimidine. The residue was dissolved in boiling ethanol, and treated with decolorizing charcoal. The solution was evaporated to about 50 ml, and then diluted with 50 ml of water. The solid was separated by filtration, and suspended in 100 ml of water to which 50 ml of 10 percent aqueous sodium hydroxide solution was then added. The mixture was filtered, and the filtrate was cooled and then neutralized with concentrated hydrochloric acid. The resulting yellow solid was washed with water and a small amount of diethyl ether, and was dried to provide 7-chloro-3-(n-propyl)imidazo[1,5-c]pyrimidin-5-one, m.p. 194°–196° C. Analysis: Calculated for $C_9H_{10}ClN_3O$: %C, 51.1; %H, 4.8; %N, 19.9; Found: %C, 51.1; %H, 4.7; %N, 20.1.

EXAMPLE 6

To a mixture of 40 g of 2-hydroxy-6-methyl-4-pyrimidinecarbaldoxime and 400 ml of water was added 120 g of stannous chloride hydrate in 400 ml of concentrated hydrochloric acid. The mixture was stirred for about sixteen hours at 20° C. Partial evaporation provided a residue which was mixed with 120 ml of acetic anhydride and 10 g of sodium acetate. The mixture was heated on a stream bath for 0.5 hour, and was then allowed to cool. The solid was collected by filtration and washed with acetone. The solid was suspended in 200 ml of water and the mixture was neutralized with concentrated ammonium hydroxide. The solid was separated by filtration and suspended in boiling methanol. The insoluble residue was separated by filtration and discarded. The filtrate was evaporated, and the residue obtained was dissolved in boiling acetone and treated with decolorizing charcoal. The solution was then evaporated to provide a residue which was recrystallized twice from acetone with treatment with decolorizing charcoal to provide white crystals of 3,7-dimethylimidazo[1,5-c]pyrimidin-5-one, m.p. 231°–232° C. Analysis: Calculatd for $C_8H_9N_3O$: %C, 58.9; %H, 5.6; %N, 25.8; Found: %C, 58.9; %H, 5.5; %N, 25.7.

EXAMPLE 7

To a mixture of 25 ml of N,N-dimethylformamide and 1.5 g (0.03 mole) of 50% sodium hydride in oil was added 4.9 g (0.03 mole) of 3,7-dimethylimidazo[1,5-c]pyrimidin-5-one (from Example 6). The reaction to form the sodium salt was exothermic. After the exotherm subsided, 5.1 g (0.03 mole) of benzyl bromide was added dropwise. The stirred mixture was heated at 80° C. for sixteen hours, and was then evaporated. The residue was mixed with water, and then extracted with chloroform. The organic layer was washed with water, dried and evaporated. The residue was triturated with a 50/50 methanol/ethyl acetate mixture, and the solid was separated by filtration. Recrystallization from cyclohexane with treatment with decolorizing charcoal provided white crystals of 6-benzyl-3,7-dimethylimidazo[1,5-c]-pyrimidin-5-one, m.p. 128°–129° C. Analysis: Calculated for $C_{14}H_{15}N_3O$: %C, 71.1; %H, 6.0; %N, 16.6; Found: %C, 71.1; %H, 6.1; %N, 16.3.

EXAMPLES 8–9

Using the method of Example 7, 3,7-dimethylimidazo[1,5-c[pyrimidin-5-one was reacted with various alkyl halides to provide the compounds of the invention shown below:

| Ex. No. | Alkyl Halide | Product of Formula I | Melting Point (in °C.) | Recrystallization Solvent |
|---|---|---|---|---|
| 8 | CH₃(CH₂)₂Br | [structure: CH₃(CH₂)₂N-C(=O)-N ring with CH₃ groups] | 156–157 | cyclohexane |
| 9 | CH₃I | [structure: CH₃-N-C(=O)-N ring with CH₃ groups] | 184–185 | ethyl acetate |

EXAMPLES 10-12

Using the method of Example 7, 3-methyl-7-methylthioimidazo[1,5-c]pyrimidin-5-one was reacted with various alkyl halides to provide the compounds of the invention shown below.

| Ex. No. | Alkyl Halide | Product of Formula I | Melting Point (in °C.) | Recrystallization Solvent |
|---|---|---|---|---|
| 10 | CH₃I | [structure with CH₃-N, CH₃S substituents] | 122–123 | cyclohexane |
| 11 | CH₃(CH₂)₂Br | [structure with CH₃(CH₂)₂-N, CH₃S substituents] | 87–88 | cyclohexane |
| 12 | [benzyl-CH₂Cl] | [structure with benzyl-CH₂-N, CH₃S substituents] | 137–140 | cyclohexane |

EXAMPLE 13

To a mixture of 2.0 g (10.9 mmole) of 7-chloro-3-methylimidazo[1,5-c]pyrimidin-5-one (from Example 4, Part B) in 50 ml of dioxane was added 0.52 g (13 mmole) of 60% sodium hydride in oil. After ten minutes of stirring, 1.6 g (13 mmole) of 3-bromopropane was added and the mixture was stirred for 16 hours at 50° C. The solution was poured into 100 ml of an ice water mixture. The resulting solution was extracted four times with 75 ml portions of chloroform. The extracts were washed twice with water, dried, and evaporated. The residue was dissolved in 80 ml of chloroform, washed with six 100 ml portions of water, dried and evaporated. The residue was recrystallized with treatment with decolorizing charcoal from cyclohexane to provide 7-chloro-3-methyl-6-n-propylimidazo[1,5-c]pyrimidin-5-one, m.p. 125°–126° C. Analysis: Calculated for $C_{10}H_{12}ClNO$: %C, 53.2; %H, 5.4; %N, 18.6; Found: %C, 53.5; %H, 5.3; %N, 18.6.

EXAMPLE 14

To a cold (0° C.) mixture of 30 ml of 50% aqueous potassium hydroxide solution and 80 ml of diethyl ether was added in small portions 10 g (97 mmole) of 1-methyl-1-nitrosourea to generate diazomethane. The organic layer was separated and added to a mixture of 6.00 g (32.7 mmole) of 7-chloro-3-methylimidazo[1,5-c]pyrimidin-5-one (from Example 4, Part B) in 100 ml of a 1:1 mixture of ethanol/diethyl ether. Several more portions of diazomethane were obtained by adding ether to the aqueous potassium hydroxide, followed by separation of the organic layer. These portions were added to the reaction mixture until the total volume was about 400 ml. The reaction mixture was stirred for 16 hours with the starting temperature initially at 0° C., but gradually being allowed to rise to about 20° C. The solid was separated by filtration. The filtrate was evaporated to provide a residue. The solids were combined and separated into fractions by high pressure liquid chromatography, eluting sequentially with dichloromethane, 5% ethyl acetate/dichloromethane and 1:1 ethyl acetate/dichloromethane. Early fractions contained small amounts of pure white solid 7-chloro-5-methoxy-3-methylimidazo[1,5-c]pyrimidine, m.p. 108°–110° C. Analysis: Calculated for $C_8H_8ClN_3O$: %C, 48.6; %H, 4.1; %N, 21.3; Found: %C, 48.3; %H, 3.9; %N, 21.1. The structural assignment was confirmed by infrared and nuclear magnetic resonance spectral analyses. Middle fractions were mixtures and later fractions contained white solid 7-chloro-3,6-dimethylimidazo[1,5-c]pyrimidin-5-one, m.p. 165°–166° C. after recrystallization from 5:3 benzene/hexane. Analysis: Calculated for $C_8H_8ClN_3O$; %C, 48.6; %H, 4.1; %N, 21.3; Found: %C, 48.7; %H, 4.0; %N, 21.4.

What is claimed is:

1. A compound of the formula

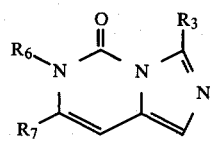

wherein $R_3$ is hydrogen, lower alkyl or phenyl, $R_6$ is hydrogen, lower alkyl, or benzyl; and $R_7$ is chloro, lower alkoxy, lower alkylthio, or methyl; or a pharmaceutically acceptable acid addition salt thereof.

2. A compound according to claim 1, wherein $R_6$ is lower alkyl.

3. The compound 3-methyl-7-methylthio-6-(n-propyl)imidazo[1,5-c]pyrimidin-5-one according to claim 1.

4. The compound 3-methyl-7-methylthioimidazo[1,5-c]pyrimidin-5-one according to claim 1.

5. The compound 7-chloro-3-(n-propyl)imidazo[1,5-c]pyrimidin-5-one according to claim 1.

6. The compound 7-chloro-3-methyl-6-(n-propyl)imidazo[1,5-c]pyrimidin-5-one according to claim 1.

7. The compound 3,7-dimethyl-6-(n-propyl)imidazo[1,5-c]pyrimidin-5-one according to claim 1.

8. The compound 6-benzyl-3,7-dimethylimidazo[1,5-c]pyrimidin-5-one according to claim 1.

9. The compound 6-benzyl-3-methyl-7-methylthioimidazo[1,5-c]pyrimidin-5-one according to claim 1.

10. The compound 3,6-dimethyl-7-methylthioimidazo[1,5-c]pyrimidin-5-one according to claim 1.

11. A pharmaceutical composition comprising an effective amount of a compound according to claim 1 and a pharmaceutically acceptable carrier.

12. A method for obtaining bronchodilation in a mammal wherein an effective amount of a compound according to claim 1 is administered to a mammal.

13. A method according to claim 12 wherein the compound is administered by inhalation.

* * * * *